(12) United States Patent
Menzel

(10) Patent No.: US 7,910,376 B2
(45) Date of Patent: Mar. 22, 2011

(54) METHOD FOR DETECTING TRACE EXPLOSIVES USING PHOTOLUMINESCENCE

(75) Inventor: Roland E. Menzel, Lubbock, TX (US)

(73) Assignee: Alexander Menzel, Hermosa Beach, CA (US)

(*) Notice: Subject to any disclaimer, the term of this patent is extended or adjusted under 35 U.S.C. 154(b) by 866 days.

(21) Appl. No.: 10/558,330

(22) PCT Filed: May 21, 2004

(86) PCT No.: PCT/US2004/015973
§ 371 (c)(1),
(2), (4) Date: Feb. 27, 2007

(87) PCT Pub. No.: WO2004/106907
PCT Pub. Date: Dec. 9, 2004

(65) Prior Publication Data
US 2008/0044909 A1 Feb. 21, 2008

Related U.S. Application Data

(60) Provisional application No. 60/473,434, filed on May 27, 2003.

(51) Int. Cl.
*G01N 21/76* (2006.01)
(52) U.S. Cl. ..... 436/172; 436/110; 436/111; 422/82.07; 359/342
(58) Field of Classification Search ............ 436/110, 436/111, 172; 422/82.07; 356/342
See application file for complete search history.

(56) References Cited

U.S. PATENT DOCUMENTS

| | | | | |
|---|---|---|---|---|
| 5,296,380 A | * | 3/1994 | Margalit | 436/106 |
| 5,818,047 A | * | 10/1998 | Chaney et al. | 250/341.8 |
| 6,331,438 B1 | * | 12/2001 | Aylott et al. | 436/172 |
| 2002/0015150 A1 | | 2/2002 | Armstrong et al. | |

FOREIGN PATENT DOCUMENTS

| | | |
|---|---|---|
| JP | 2002-505426 | 2/2002 |
| JP | 2002-286639 | 3/2002 |
| JP | 2006-500627 | 1/2006 |
| WO | WO 02/06277 | 1/2002 |

OTHER PUBLICATIONS

Dexter McRae et al. "High Explosive Spot Test Analyses of Samples from Operable Unit (OU) 1111", DOE Technical Report, U.S.A., Report No. LA-12753-MS, 1995, pp. 1-23.
Joseph Almog et al. "ETK—An Operational Explosive Testing Kit", Journal of Energetic Materials, 1986, vol. 4, No. 1-4, pp. 159-167.

* cited by examiner

*Primary Examiner* — Lyle A Alexander
(74) *Attorney, Agent, or Firm* — Fulbright & Jaworski L.L.P.

(57) ABSTRACT

A method for detecting trace explosives which includes obtaining a sample believed to contain explosives residue and contacting the sample and a carrier container containing the sample with a reagent. The sample and the carrier is illuminated by an appropriate laser or other light source while it is contained within a light tight box. The sample and the carrier is observed during the elimination to determine photoluminescence of the sample as an indication that it contains trace explosives. The reagent may be an alkaline containing substance, a lanthanide complex, a lanthanide complex containing sensitizing ligands or nanocrystals.

15 Claims, No Drawings

METHOD FOR DETECTING TRACE EXPLOSIVES USING PHOTOLUMINESCENCE

CROSS-REFERENCE WITH RELATED APPLICATIONS

This application claims the benefit of U.S. Provisional Application No. 60/473,434 filed on May 27, 2003.

FIELD OF THE INVENTION

The present invention relates generally to the detection of trace explosives and more particularly to a method for field use determination of traces of explosives utilizing laser or other light source induced photoluminescence.

BACKGROUND OF THE INVENTION

The increased use of explosives by terrorists is posing serious problems to law enforcement agencies, security personnel and airport authorities. Sending of explosive devices even as letter bombs, package bombs, or luggage bombs through the mail and the use of explosive devices against both the civilian and military population has increased throughout the world.

It is known that small quantities of explosives are transferred to the hands during contact with commercial explosives or alternatively may be deposited on the outer surface of letter bombs and packages during the preparation of the explosive device. Furthermore, small quantities of explosives may also be deposited upon the surfaces of tables, benches or other supporting structures used in constructing bombs or other explosive devices. Most explosives used in the preparation of such a device have sufficient vapor pressure at ambient conditions to diffuse traces of those explosives to the surface. The detection of explosives in airport terminals, government buildings, embassies, aircraft, and vehicles requires simple portable and economical devices that can give a quick and positive identification of the presence of traces of explosives residue.

As a result of interest in this area, numerous methods and devices have been developed to reduce the risk to the general population by detecting the presence of said materials and preventing their use. The techniques previously employed include X-ray detection and nuclear techniques such as thermal neutron analysis and nuclear resonance absorption. These techniques have been found to be applicable in the sensing of concealed energetic materials found in luggage or other containers. However, it is extremely difficult to detect the presence of dangerous chemicals such as explosives when carried by a person. Due to the health risks and exposing a human to X-rays and nuclear techniques, authorities are unable to monitor people in the same fashion or as thoroughly as they can luggage or other containers.

As a result, other prior art methods do exist which serve the purpose of detecting the presence of the target compounds vapors in the atmosphere. Among the prior art vapor sensing techniques employed are gross chromatography/chemiluminescence, quadrupole mass spectrometry, ion mobility spectrometry, and animals such as sniffing dogs.

Although these techniques appear attractive, since they are capable of atmospheric vapor analysis their applications are limited. For instance, when one employs the sensing method of gas, chromatography/chemiluminescence, the response time before the results are obtained is lengthy while quadrupole mass spectrometry is limited in that it suffers from non-selective ionization, that is, all the species entering the ionization region are ionized and transmitted into the mass spectrometer. The additional technique of ion mobility spectrometry is extremely sensitive and has a relative short response time. However, this method is not quantitatively as accurate as the others since the signal dependence on concentration is non-linear. Moreover clustering of the target molecules with water and low mass spectroscopic resolution are problems frequently encountered.

In addition, the use of laser technology has been employed for the detection of trace atmospheric nitro compounds. A sample of the atmosphere containing the suspected compounds is subjected to a laser which operates at or near 226 nm. to photodissociate the target module into $NO_2$ and its companion radical and thereafter the detection of the characteristic fragment NO by resonance-enhanced multi-photon ionization and/or laser-induced-fluorescence. Although this technique also appears attractive, it requires the utilization of equipment capable of utilizing a pulsed nozzle to accomplish the desired gas through put entering the analysis chamber and thus requires expensive and difficult to operate equipment.

An additional explosive detection kit and method for detecting trace explosives utilizes the technique of providing a sample from a suspect source and then contacting the sample with a plurality of reagents one after the other for the purpose of generating a distinct coloration associated with explosive materials. This process is more suitable for operation by non-skilled personnel such as guards, police officers, and soldiers in airports, boarder crossings, bus station and buses for a simple and quick detection of explosives.

As the use of explosives by terrorists become an ever growing problem worldwide, it is widely recognized that there is a need for and it would be highly advantageous to have a method and device which can be accurately operated by non-skilled personnel with a device that will provide a highly sensitive detection of trace explosives.

SUMMARY OF THE INVENTION

A method for detection of trace explosives which includes isolating a sample from an appropriate source thereof, applying an appropriate reagent to the sample, illuminating the sample with a light source (excitation) and observing the photoluminescence of the sample. Photoluminescence refers to the emission of light either as fluorescence or phosphorescence produced by prior absorption of light of a shorter wavelength than that of the emitted light.

DETAILED DESCRIPTION OF THE INVENTION

The vast majority of explosives of concern belong to one of the four following chemical categories:
1. Polynitro aromatics such as 2,4,6-trinitrotoluene (TNT), 2,4-dinitrotoluene (DNT), picric and its derivatives;
2. Nitrocellulose (HMX and smokeless powder), nitroglycerine (NG), cyclotrimethyllenetrinitramine (RDX);
3. Inorganic nitrates such as black powder or ANFO (a mixture of ammonium nitrate and fuel oil);
4. Inorganic chlorates or bromates.

Colorimetric explosives detection of these types of explosives are accomplished through the utilization of alkali-based reagents which when applied to the explosives yield a reddish color in most instances. Category 4 explosives usually develop a blue color.

Applicant has discovered that when such explosives treated with the typical reagents existing in the known art are subjected to illumination by a laser or other light source the resultant is luminescence which increases the sensitivity gain factor from that without the luminescence by a surprising amount, up to three factors of 10 gain in sensitivity.

Commercial test kits are available on the market at the present time and include readily-available reagents which react with the classes of explosives typically available to terrorists and which are the subject for detection by use of the present invention. One such readily-available test kit is fully disclosed in U.S. Pat. No. 5,296,380 issued Mar. 22, 1994 to Yair Margalit and entitled Method and Kit for Detecting Explosives and this patent by this reference is incorporated into this application in its entirety.

As is therein disclosed, four different reagents A, B, C and D are utilized for application to a filter paper or similar carrier of suspected trace explosives. Each of the reagents is capable of bonding with specific explosives and when such occurs produces a coloration indicative of the explosives. The resultant of the explosive with the reagent when subjected to illumination by a laser or similar light source then photoluminesces and provides enhanced sensitivity enabling very positive identification of the existence of a trace explosive. The particular reagents and the explosives for which they are designed are as follows:

Reagent A

For Nitroaromatics

Sulfanilamide (20 g) is dissolved in a magnetically stirred mixture of DMSO (700 ml) and 5% KOH in 40:60 methanol/isopropyl alcohol (300 ml); if a small amount of residue remains, the liquid phase may be decanted or filtered, prior to transfer to storage and filling ampoules. This reagent gives a pink to red or violet-red coloration with nitroaromatics such as TNT, DNT, TNB or tetryl (sensitivity to about $5\times10^{-4}$ mg), and a yellow color with picric acid or its salts (sensitivity $10^{-3}$ mg).

Reagent B

For Organic Esters of Nitric Acid and Nitramines

N-(1-naphthyl)ethylenediamine (3 g) is added to a magnetically stirred mixture of 85% phosphoric acid (100 ml) and twice-distilled water (900 ml), followed by hydrazine sulfate (5 g) and sodium thiosulfate pentahydrate (0.5 g). (It is presently contemplated that metabisulfite or ascorbic acid might be used additionally or in the alternative, as nitrate to nitrite ion reducing agents). Active carbon (1 g) is added and stirring is continued for a further 15 minutes, after which the mixture is filtered, prior to transfer to storage and filling ampoules. This reagent gives a violet to red coloration with nitrate ester or nitramine explosives such as dynamite, HMX, smokeless powder, nitroglycerine, PETN, RDS, C4 and Semtex. The sensitivity of this test is in the range $10^{-4}$ to $10^{-5}$ mg.

Reagent C

For Inorganic Nitrates

To a mixture of magnetically stirred DMSO (600 ml) and isopropyl alcohol (400 ml), there is added zinc power (20 g) which had previously been finely ground in a mortar. Stirring is stopped after 10 minutes. After allowing to stand for a further 10 minutes, the desired supernatant, which is a turbid grey liquid, is decanted from the residue of coarse zinc particles, and poured into a storage vessel prior to being used for filling ampoules. The thus-prepared emulsion containing zinc is very stable to light and under normal conditions; the ampoules do not need to be colored. This reagent gives a violet-red or red coloration with nitrates and is sensitive to as little as $10^{-5}$ mg of nitrate.

Reagent D

For Chlorates or Bromates

A liquid mixture is first prepared by carefully adding 95% sulfuric acid (400 ml) to a mixture of DMSO (90 ml), ethanol (100 ml) and water (500 ml). Aniline sulfate (23 g) is then added with stirring to the liquid mixture until a homogeneous solution is obtained. The thus-prepared reagent is poured into a storage vessel prior to being used for filling ampoules. It is very stable to light and under normal conditions; the ampoules do not need to be colored. This reagent gives a strong blue coloration with chlorates within 10-20 seconds, which fades on standing; it is sensitive to as little as $2\times10^{-2}$ mg of chlorate. A blush-pink color is obtained in the presence of bromate; perchlorate does not give a positive reaction.

To perform sensitivity studies, samples of the target materials were obtained. Filter paper was then spotted with a sample of the explosive of interest. Thereafter a reagent of the type above-described was applied to the spot of explosive. At the same time to provide a control, a drop of the reagent was also applied to the filter paper apart from the area where the specimen of explosive existed. Observation was then made of the sample to determine whether or not it assumed a desired color as described above with regard to the reagent. Thereafter, the sample and the control was inserted into a compact light type box to which an appropriate laser was attached. The box included a viewing port equipped with an appropriate filter to block reflected laser light and to permit transmission of the fluorescence of interest. The laser then illuminated the sample and the control and the results were observed. The laser (130 mW) was operated at 532 nm. It was observed that the sensitivity was improved by at least two orders of magnitude as compared to the normal calorimetric sensitivity. The photoluminescence detection mode does not distinguish between category 1 and category 2 explosive because photoluminescence develops only once reagent B is applied. For photoluminescence detection of category 4 explosive, reagent D is followed by reagent B, unlike in the normal colorimetric protocol. This changes the color of the product from blue to orange. The orange product, in turn, is photoluminescent under green excitation.

The light source utilized to accomplish the photoluminescence must deliver the appropriate color to be absorbed by the material of concern. It is desirable that the light source be battery-operated and easy to utilize by untrained individuals in the field. There are in existence commercially available light sources such as frequency-doubled CW (as opposed to pulsed) Nd:YAG (or Nd:YVO$_4$) lasers which delivered green light at 532 nm and are battery-operated flashlight-size and operated with flashlight ease. There are also inexpensive handheld ultraviolet lamps. These can operate either in the near UV (wavelength greater than 300 nm or deep UV wavelength less than 300 nm spectral ranges. There are turn-key UV lasers that operate at 355 nm and that may be powered from batteries. Finally, the use of light-emitting diodes and flash-lamps is envisioned. The chemistries currently used in calorimetric detection of explosives mostly yield blue, pink-red, red, or red-violet test spots as above indicated in the discussion of the various reagents described in U.S. Pat. No. 5,296,380. If these colored products were photoluminescent, they would call for orange red excitation in the case of blue products and blue-green excitation in the case of the reddish products. Explosive detection chemistries that respond to UV excitation also are possible in this application. Emphasis is placed on photoluminescent methods that respond to green or UV excitation. The following table shows typical sensitivity gains realized for various explosives when using the photoluminescence method of the present invention.

| Expl. type | Explosive | Sensitivity gain (factors of ten) |
|---|---|---|
| I | 2,4 dinitrotoluene | 3 |
|  | trinitrotoluene | 2 |
| II | RDX | 2 |
|  | HMX | 3 |
|  | C4 | 2 |
|  | nitroglycerin | 2 |
|  | smokeless powder | 2 |
| III | ANFO | 2 |
|  | black powder | 2 |
| IV | potassium chlorate | 1 |

Under certain circumstances involving the detection of traces of explosives in situ background color or background fluorescence may mask the detection of the explosive. It then becomes of interest to detect the explosive by time-resolved photoluminescence techniques in order to suppress the background. It has been found that by tagging of the explosive with lanthanide elements and then to use a time-resolved detection apparatus such is achieved.

The lanthanide elements typically exist in compounds in the trivalent state. Some of them, most notoriously europium and terbium, $Eu^{3+}$ and $Tb^{3+}$, luminesce with high quantum efficiency. The most intense luminescence of the europium ion occurs at about 615 nm (red), arising from the transition from the upper $^5D_0$ to the lower $^7F_2$ state. For terbium, the corresponding states are $^5D_4$ and $^7F_5$, respectively, with green luminescence at 545 nm. Although the luminescence efficiencies can be high, the luminescence intensities are generally quite low because the lanthanide molar extinction coefficients (proportional to the ion's ability to absorb light) are very low because the transitions from the ground state ($^7F_o$ for the europium and $^7F_6$ for the terbium ion) are both parity- and spin-forbidden. Moreover, many lanthanide compounds include waters of hydration and these quench the lanthanide photoluminescence via coupling of the O-H vibrational overtones to the lanthanide electronic states in much the same way as molecular vibrations couple to electronic states to quench molecular fluorescence via the well-known internal conversion and intersystem crossing mechanisms. The severity of the quenching is proportional to the number of waters of hydration in the compound. It is known that very intensely luminescent lanthanide compounds can be prepared by binding to the lanthanide ion organic ligands that (a) occupy all binding sites of the lanthanide ion, thereby excluding waters of hydration, and (b) absorb well and then transfer this excitation energy to the lanthanide ion (much more effectively than direct absorption by the lanthanide ion itself) via the Forster energy transfer process. Typically, the excitation of the lanthanide (either europium or terbium) complex is in the ultraviolet (to the ligand and from there to higher lanthanide states via the Forster process, followed by radiationless decay within the lanthanide ion to the lower-lying emitting lanthanide excited state, followed by the lanthanide luminescence). Action by the ligand corresponding to the direct energy transfer of the excitation to the emitting state (579 nm for the europium and 488 nm for the terbium) is not effective because this (lower) excited state does not couple well to ligand states (on parity grounds), hence is not readily amenable to the ligand-lanthanide energy transfer. The absorbing ligand that transfers the excitation energy to the lanthanide ion is often referred to as a sensitizing ligand. One example of such is shown as:

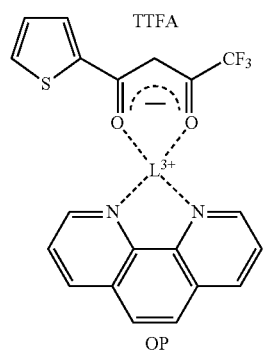

In colorimetric detection schemes, the pertinent properties of light (via absorption/reflection) are color and intensity. In photoluminescence schemes, the pertinent properties of the emitted light are color and intensity as well, but there is now a third property that can be exploited, namely luminescence lifetime, the time of decay of the luminescence once the excitation (illumination) is shut off. Lifetimes of typical molecular fluorescences are on the order of a nanosecond. Phosphorescences have much longer lifetimes. The lanthanide luminescences rightly can be classified as phosphorescences, because of their long lifetimes, of millisecond order, and because the two states involved in the emission process have different spin multiplicities. The long lanthanide luminescence lifetimes permit detection in the presence of strong background fluorescence by time-resolved techniques and thus are especially interesting, not only in the forensic science context but in many other fields as well.

Lanthanides have nine-fold full coordination. This is easily seen by noting that common lanthanide salts are of the form $LX_3 \cdot 6H_2O$, where L is the trivalent lanthanide cation ($Eu^{3+}$ or $Tb^{3+}$ for example), X is a monovalent anion (chloride or nitrate most often), with 6 water molecules completing the coordination. The bonding of the water to the lanthanide ion, through the oxygen end of the water, is neither ionic nor of the typical covalent bonding variety of organic molecules. It has some electrostatic characteristics, namely the attraction between a charged object and an electric dipole, which is reminiscent of hydrogen bonding, and some covalent characteristics as well. Many of the organic ligands useful for making highly luminescent lanthanide complexes are bidentate (occupying two coordination sites). Thus, four such ligands only can bind to the lanthanide, leaving one free coordination site, which may remain unoccupied if the ligands are large, so that steric hindrance precludes access by water, or another kind of ligand, to this last site, or the site is occupied by a monodentate ligand. The one of most concern here is water, a notorious lanthanide luminescence quencher. One water of hydration may still be tolerable, but a larger number of waters of hydration very seriously degrades lanthanide luminescence, the quenching being proportional to the number of hydration waters. When lanthanides form coordination complexes, they show a preference for binding to oxygen, as in water, for instance. This preference may increase further when the oxygen acts as if it were a negatively charged entity, as it does in most explosives via the ubiquitous $NO_2$ functionality. The proclivity of lanthanides for water is such that a number of lanthanide complexes that are highly luminescent are quenched once placed in the presence of water because the water displaces the sensitizing ligands.

$Eu(TTFA)_4$, $Eu(OP)_4$ and the corresponding terbium complexes were prepared quite simply by mixing the commercially available lanthanide chloride hexahydrate salt and TTFA or OP in methanol. A five-fold excess of ligand was used over the 1:4 lanthanide:ligand stoichiometric proportion. The resulting concentration of the complex was about $3 \times 10^{-4}$M. The chromatography paper spotted with the explosive was then immersed for a second or two in the methanol solution of the lanthanide complex, or was spotted with the lanthanide complex solution. When the paper was then left to dry for a minute or two with OP and smokeless powder, under the deep UV excitation pertinent to OP. There was observed around the intensely luminescent (red) region where the explosive is located a light blue-luminescent halo, which arises either from displacement of residual water from the explosive spot region via the methanol solvent or from migration of the excess OP used in the formulation of the lanthanide complex. In the halo region, that water, in turn, would displace ligands from unreacted complex to quench luminescence and/or the excess OP would dominate the luminescence of the halo region. Thus, in the halo region the observed luminescence was that of free OP (light blue). Farther out from the halo region, intense (red) luminescence from unreacted lanthanide complex was seen, together with the light blue luminescence of free OP due to the excess of OP in the formulation of the lanthanide complex. The overall effect in this region was the observation of a pinkish red. When the sample was inspected through a band-pass filter tuned to the red europium emission (wedge filter), no luminescence was seen from the halo region and the explosive spot region and the region of unreacted complex showed the same intensity, at least to the level of what could visually be discerned. Once the sample was subsequently rinsed in running tap water for a few seconds (or was simply immersed briefly in water), the result was no luminescence seen from unreacted complex. It is not necessary to let the paper dry before observation, nor is it necessary to let the paper dry for any length of time after the prior methanol spotting or immersion. Thus, the procedure is quite quick. The illumination employed a hand-held UV lamp (Model UVGL-58, Mineralite® Lamp, UVP, Upland, Calif.) operating in the deep UV. Similar results were obtained with RDX and with the corresponding green emitting terbium complex for both explosive samples. Results were similar with the corresponding TTFA complexes. With the advent of photoluminescent semiconductor nanocrystals, also referred to as quantum dots, nanoparticles or nanocomposites direct sensitization is possible. This direct sensitization is accomplished for europium via CdS nanocrystals and CdSe nanocrystals, mostly referred to as quantum dots (Qdots). Those Qdots emitt in the orange, as needed for the requisite spectral overlap with the emitting europium state. The Qdots may be used by binding to the lanthanide. However, the donor-acceptor energy transfer is not actually dependent on chemical binding. It suffices that the donor and acceptor be in close proximity. The energy transfer efficiency depends on $R^{-6}$, where R is the distance between the donor and the acceptor. Of course, chemical binding is ideal because then small R is assured. Europium complexes, namely Eu-TTFA (thenoyltrifluoroacetone) and Eu-OP (ortho-phenanthroline) were prepared in methanol solution, at a concentration of 3 millimolar. The ligands are there only to exclude the luminescence-quenching water, rather than to serve as sensitizers. The complexes were spotted (one drop) on an appropriate carrier. Qdot™ 585 Streptavidin Conjugate was obtained from Quantum Dot Corp. This is a water suspension of the Qdots, and was used as received, without the accompanying buffer solution. It was spotted directly in one drop quantity over the Eu spots on the TLC plate. Control Eu spots and Qdot spots alone were also applied as controls.

The Qdots respond to both UV and green excitation. Under UV excitation, the luminescence (control and other spots) was astoundingly intense, very much more intense than that of the control Eu spots. Under 532 nm green excitation the Qdots continued to exhibit very intense emission, whereas the Eu control spots exhibited no luminescence at all, as to be expected. The Qdot luminescence peaked at 590 nm with full width at half maximum of 32.5 nm. In terms of donor-acceptor overlap at 579 nm, one is thus still at 70% of maximum donor luminescence intensity. However, at the Eu emission wavelength, about 615 nm, one is still at 30% of maximum Qdot luminescence, which represents a very large background emission intensity if one seeks Eu emission resulting from energy transfer. We thus anticipated having to employ time-resolved spectroscopy to suppress this background in order to dig out from underneath the anticipated much weaker Eu luminescence. On standard luminescence spectroscopy, under the 532 nm excitation, as clearly defined shoulder at the right wavelength (about 615 nm) and of the right width (about 5 nm) was found in the overlayed spots but not in the Qdot control spot (the Eu control spots not exhibiting any luminescence at all). This represented a Qdot-to-Eu energy transfer yielding Eu emission of intensity computed to be 4% of the maximum Qdot emission intensity. We construe this as impressive energy transfer, considering that the above-discussed R proximity between Qdot and Eu was not achieved by chemical binding but by merely placing drops over each other on porous substrates. It is noted that the streptavidin conjugate is a large moiety (roughly 60 kDa) so that the proximity between the europium ion and the quantum dot itself suffers. Using a simple mechanical light chopper-based apparatus, direct time-resolved visualization by eye of the characteristic red europium emission was nonetheless achieved under 532 nm excitation. No europium luminescence was found under 532 nm excitation with the chloride, OP and TTFA europium compounds. Under UV excitation (355 nm) by laser (15 mW) a sensitivity gain of an order of magnitude over the colorimetric sensitivity was achieved (in above discussed indicate that the corresponding first-generation field device utilizing the the non-time-resolved mode) when RDX as a typical example was tagged with Eu/TTFA. The laser was actually a pulsed laser, operating at 6 kHz. Given the long europium luminescence lifetime, about 0.4 ms, however, the laser acts as if it were CW to permit the simple standard or mechanical light chopper-based time-resolved visualization. Results were similar with the corresponding TTFA complexes under near-UV excitation.

In the field detection scenario one places the trace explosive collecting swab, after chemical treatment (as in the usual field-testing procedure), in a (small) light tight box with ports for the light source and for a filter-equipped eye piece for viewing. The device is easy to build, compact, and not expensive (excepting the light source). Our results with the reagents battery-operated laser mentioned earlier is practically viable. One may imagine situations in which the field detection of trace explosive is to be done in situ (rather than by swabbing). Here, the lanthanide approach is of value in that time-resolved visualization allows the elimination of the background color or fluorescence (when optical filtering is ineffective). Given the long luminescence lifetimes of lanthanides, this is not difficult to accomplish. The simple light chopper device accomplished this. The chopper can easily be designed to provide the appropriate triggering to a proximity-focused microchannel plate image intensifier placed at the eye piece location of the above light-tight box and the time-resolved image is seen on the phosphor screen of the image intensifier, if sensitivity higher than that of visualization by eye is desired. Alternatively, an intensified OCD camera could be used. The light chopper blade would have two sets of openings, one to chop the exciting light and the other to provide the appropriate gate delay and gate width to the image intensifier via a light emitting diode (LED)—photosensor pair with associated electronics as well known in the art. In comparison with the above routine version of the device, one now has the added expense of the chopper and if desired, intensifier but it is unlikely that the time-resolved version would need to be deployed as widely as the routine version.

The advent of photoluminescent nanocrystals and nanocomposites offers additional prospects in the explosives arena. Here, one can foresee direct photoluminescence detection of explosive traces tagged with such nanoparticles, functionalized chemically with conjugating ligands to bind to the explosive. One would then have a nanoparticle method akin to the lanthanide method, in the above routine implementation, or in an appropriate time-resolved modality in which the mechanical light chopper would be replaced by an electro-optical modulator or in which the laser/light chopper combination would be replaced by a pulsed laser, such as a frequency-tripled Nd:YVO$_4$ laser operating at 355 nm. Such lasers have suitably short pulse widths (commensurate with $10^{-8}$-$10^{-6}$ s nanoparticle luminescence lifetimes), high repetition rates (tens of kHz), provide average powers ranging from 100 mW to Watts, and operate on ordinary household current. In terms of the above lanthanide strategy, these lasers act as if they were CW, given the long lanthanide luminescence lifetimes, and would be used directly, or together with the above-discussed simple mechanical light chopper for time-resolved purposes. The powers they provide are orders of magnitude larger than what one gets from the hand-held UV lamps discussed above, hence greatly aid explosives detection sensitivity.

What is claimed is:

1. A method for detecting trace explosives comprising:
   isolating a sample containing the trace explosive;
   contacting the sample with a reagent, said reagent being a lanthanide complex having sensitizing ligands;
   placing the sample/reagent in an enclosure, the enclosure having a first port and a second port;
   illuminating the sample/reagent with a laser or other light source through the first port;
   observing the photoluminescence emitted by the sample/reagent through the second port; and,
   using one or both of photoluminescence intensity and photoluminescence lifetime to detect said trace explosives.

2. The method as defined in claim 1 wherein the reagent is an alkaline based reagent.

3. The method as defined in claim 1 wherein the laser operates in the near ultraviolet.

4. The method as defined in claim 1 wherein the laser operates at 532 nm.

5. The method as defined in claim 1 wherein the reagent is a nanocrystal.

6. The method as defined in claim 1 in which the light source is one operating in the green wavelength.

7. The method as defined in claim 6 in which the light source is a green laser operating at 532 nm.

8. The method as defined in claim 1 wherein the sensitizing ligands are replaced with a nanocrystal.

9. The method as defined in claim 8 wherein the nanocrystal is CdSe.

10. A method for detecting trace explosives comprising:
    isolating a sample containing the trace explosive;
    contacting the sample with a lanthanide complex reagent;
    placing the sample/reagent in an enclosure, the enclosure having a first port and a second port;
    illuminating the sample/reagent with a laser or other light source through the first port;
    observing the photoluminescence emitted by the sample/reagent through the second port, wherein said step of observing the photoluminescence comprises time resolved observation of the emitted photoluminescence, wherein said time resolved observation comprises measurement of photoluminescence lifetime; and;
    using said photoluminescence lifetime measurement to detect said trace explosives.

11. The method as defined in claim 10, wherein the reagent is a lanthanide complex having sensitizing ligands.

12. The method as defined in claim 11, wherein the lanthanide complex is a europium complex.

13. The method as defined in claim 10, wherein the sensitizing ligands are replaced with a nanocrystal.

14. The method as defined in claim 13, wherein the nanocrystal is CdSe.

15. The method as defined in claim 10, wherein the time resolved visualization techniques include interrupting the illumination with a light chopper.

* * * * *